United States Patent [19]

Hodakowski et al.

[11] Patent Number: 4,780,458
[45] Date of Patent: Oct. 25, 1988

[54] PHOSPHOROUS ESTERS OF CYANOHYDRINS

[75] Inventors: Leonard E. Hodakowski, Raleigh; Hafez M. Ayad, Cary, both of N.C.

[73] Assignee: Rhone-Poulenc Nederlands B.V., Amstelveen, Netherlands

[21] Appl. No.: 653,048

[22] Filed: Sep. 21, 1984

Related U.S. Application Data

[60] Division of Ser. No. 369,307, Apr. 16, 1982, Pat. No. 4,496,493, which is a continuation-in-part of Ser. No. 169,285, Jul. 6, 1980, abandoned.

[51] Int. Cl.$^4$ ............................................. A01N 57/00
[52] U.S. Cl. .................................. 514/112; 514/86; 514/89; 514/95; 514/99
[58] Field of Search .............. 424/200, 202, 203, 210; 514/86, 89, 95, 99, 112

[56] References Cited

U.S. PATENT DOCUMENTS

| | | | |
|---|---|---|---|
| 2,960,525 | 11/1960 | Dorken et al. | 260/940 |
| 2,965,533 | 12/1960 | Whetstone | 360/940 |
| 3,117,151 | 1/1964 | Blair | 260/940 |
| 3,232,830 | 2/1966 | Schrader et al. | 260/940 |
| 3,876,666 | 4/1975 | Oswald et al. | 260/940 |
| 3,927,148 | 12/1975 | Oswald et al. | 260/940 |
| 4,567,168 | 1/1986 | Kruger et al. | 514/89 |

FOREIGN PATENT DOCUMENTS

| | | | |
|---|---|---|---|
| 0058864 | 9/1982 | European Pat. Off. | 424/210 |
| 1224307 | 9/1966 | Fed. Rep. of Germany | 260/940 |
| 491644 | 11/1975 | U.S.S.R. | 260/940 |

OTHER PUBLICATIONS

Hall et al., "J. Am. Chem. Soc." vol. 79, No. 7 (1957) pp. 1768–1769.

Primary Examiner—Allen J. Robinson
Attorney, Agent, or Firm—Morgan & Finnegan

[57] ABSTRACT

Novel phosphorous esters of cyanohydrins which exhibit outstanding pesticidal activity. A method of controlling pests by subjecting the pests to a pesticidally active amount of a compound of this invention is also covered.

22 Claims, No Drawings

PHOSPHOROUS ESTERS OF CYANOHYDRINS

This application is a division of prior U.S. application Ser. No. 369,307 filed Apr. 16, 1982, now U.S. Pat. No. 4,496,493 issued Jan. 29, 1985, which is a continuation-in-part of application Ser. No. 169,284 filed July 6, 1980, now abandoned.

This invention relates to novel phosphorus esters of cyanohydrins and methods of preparing same. This invention is also directed to a pesticidal composition comprising an acceptable carrier and a pesticidally effective amount of a compound of this invention, as well as to a method of controlling pests which comprises subjecting the pests to a pesticidally effective amount of a compound of this invention.

Certain phosphate esters of cyanohydrins are disclosed in U.S. Pat. No. 2,965,533, which issued on Dec. 20, 1960 and which is assigned to Shell Oil Company. The phosphates disclosed in this patent are based on the diethyl chlorophosphate moiety:

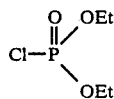
A

As an example, the patentee reacts acetone cyanohydrin with A to yield Diethyl 1-cyano-1-methyl ethyl phosphate as shown below.

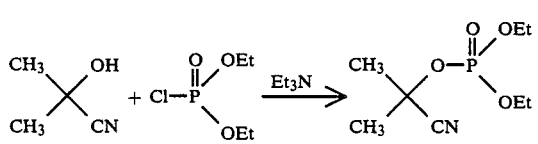

According to the present invention one of the O-ethyl groups is replaced by an S-n-propyl group which unexpectedly increases the broad spectrum pesticidal activity over the compounds disclosed in U.S. Pat. No. 2,965,533.

The novel compounds can be represented by the following generic formula:

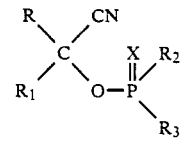

wherein X is O or S;

R and $R_1$ are the same or different and are independently hydrogen, lower alkyl ($C_1$-$C_{15}$), whereby $C_3$-$C_{15}$ can be branched or unbranched, and wherein the alkyl chain can be substituted or unsubstituted with alkylthio, alkoxy, or one or more halo; cycloalkyl ($C_3$-$C_8$), alkenyl, phenyl, benzyl, pyridinyl, pyrimidinyl, furanyl, pyranyl, naphthalene, thiophene, all of which may be optionally substituted with one or more halogen, nitro, cyano, allyloxy trihalomethyl, alkyl, alkylthio, alkoxy, or aryloxy, aryloxy alkyl, which can be further substituted with alkoxy, halogen, alkyl, or trihalomethyl groups; taken together R and $R_1$ may form a 5 or 6 membered carbocyclic ring.

$R_2$ and $R_3$ can be the same or different and are independently:
(a) alkylthio ($C_1$-$C_8$),
(b) alkoxy ($C_1$-$C_8$) with the proviso that $R_2$ and $R_3$ may not be alkoxy at the same time,
(c) thioaromatic radicals,
(d) oxyaromatic radicals,
(e) alkyl or dialkyl amino, and
(f) phenyl or benzyl which can be optionally substituted with one or more nitro, cyano, halogen, trihalomethyl, alkyl, alkoxy, alkylthio, or aryloxy.

Compositions falling within the above generic formula exhibit biological activity as pesticides to a greater or lesser extent. Some exhibit very powerful activity in extremely small dosages while other require larger dosages to be effective.

In general, the compounds which are preferred for pesticidal activity are those of the above generic formula wherein:
X is O;
R and $R_1$ are the same or different and are independently hydrogen, lower alkyl ($C_1$-$C_6$), phenyl substituted with aryloxy, further substituted with halogen;
$R_2$ and $R_3$ can be the same or different and are independently alkylthio and alkoxy ($C_1$-$C_8$) with the proviso that $R_2$ and $R_3$ may not be alkoxy at the same time.

Compounds which are most preferred are represented by nomenclature and structure as follows:

| Nomenclature | Structure |
| --- | --- |
| O—(α-Cyanobenzyl)-O—ethyl-S—n-propylthiophosphate | -O-P(=O)(OC2H5)(SC3H7)) |
| O—(2-Cyano-2-propyl)-O—ethyl-S—n-propylthiophosphate | 2C(CN)-O-P(=O)(OC2H5)(SC3H7)) |

| Nomenclature | Structure |
|---|---|
| O—(2-Methyl-1-cyanopropyl)-O—ethyl-S—propylthiophosphate | ![structure] with groups H, CH₃, CH₃, H, CN, O, OC₂H₅, O—P, SC₃H₇ |
| O—(α-Cyano-3-[2',4'-dichlorophenoxy-benzyl)-O—ethyl-S—n-propylthiophosphate | dichlorophenoxy-benzyl structure with CH(CN)—O—P(=O)(OC₂H₅)(SC₃H₇) |
| O—(1-Cyanoethyl)-O—ethyl-S—propylthiophosphate | CH₃, H, CN, O, OC₂H₅, C—O—P, SC₃H₇ |

In general, the phosphorous esters of this invention can be conveniently prepared utilizing appropriate aldehydes and ketones as starting materials. These are converted to their corresponding cyanohydrins (1–4) and then reacted with a phosphorylating group as shown below.

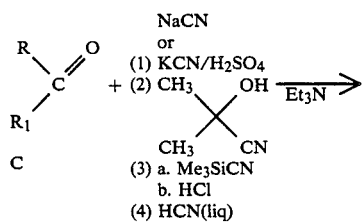

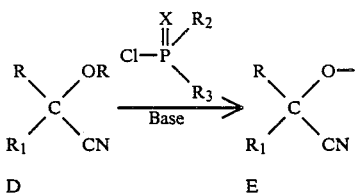

wherein the values of X, R, R₁, R₂ and R₃ are as indicated previously.

According to the above scheme, the aldehyde or ketone (C) can be converted to cyanohydrin (D) using one of the four methods listed or variations thereof. The choice of which method is used is dependent upon the substituents R and R₁.

Conversion of C→D using methods 1, 2, and 3 are detailed in Examples I, II and III.

Conversion of D→E occurs by reacting one equivalent of cyanohydrin with an appropriate chloro phosphorous compound in the presence of at least one equivalent of an acid acceptor, preferably in an inert solvent.

The acid acceptor utilized in this reaction scheme (D→E) can be either an organic or inorganic base. Illustrative of organic bases that are useful acid acceptors are tertiary amines, such as triethylamine, 4-N,N-dimethylamino pyridine, pyridine, trimethyl amine, collidine or 1,4-diazobicyclo [2.2.2] octane; bases such as sodium carbonate and potassium carbonate are illustrative of inorganic bases that are useful acid acceptors.

In general, any organic solvent that is inert to the reactants or reaction conditions may be employed in the reaction scheme shown above. Illustrative of organic solvents which are generally suitable for use in conducting these reactions are saturated, unsaturated and aromatic hydrocarbons, e.g. hexane, cyclohexane, octane, cyclohexene, dodecane, naptha, decalin, kerosene, cyclopentane, benzene, toluene, xylene, napthlene or the like; others such as dioxane, tetrahydrofuran, diethyl ether, 1,2-dimethyoxybenzen, the dialkyl ethers of ethylene glycol, or propylene glycol or chlorinated aliphatic hydrocarbons, as for example, chloroform, dichloromethane 1,1-dichloroethane, carbon tetrachloride, and the like, are also acceptable.

The reaction sequence D→E may also be conducted in a solvent which functions as an acid acceptor. Illustrative of such multifunctional solvents are N,N-dimethylaniline, pyridine, collodine or any like aromatic or heterocyclic tertiary amine compound.

The reaction sequence (C→D→E) can be conducted over a broad temperature and pressure range to yield the desired products, preferably, these reactions are conducted at a temperature of −40° C. to about 60° C. and at atmospheric or autogeneous pressure.

The phosphorous halides utilized as reactants in the scheme D→E generally are known materials which can be obtained from commercial sources or prepared in accordance with conventional methods known to those skilled in the art.

The following pesticidally active compounds are illustrative of compounds within the purview of the above generic formula and which can be conveniently prepared by the process of this invention simply by selecting appropriate reactants for use in the procedures described below.

0-(1-cyanoethyl)-0-ethyl-S-n-propylthiophosphate.
0-(2,2,2-trichloro-1-cyanoethyl)-0-ethyl-S-n-propylthiophosphate.
0-(2-methyl-1-cyanopropyl)-0-ethyl-S-n-propylthiophosphate.
0-(2,2-dimethyl-1-cyanopropyl)-0-ethyl-S-n-propylthiophosphate.

0-(2-cyano-2-propyl)-0-ethyl-S-n-propylthiophosphate.
0-(1,1,1-trichloro-2-cyano-2-propyl)0-ethyl-S-n-propylthiophosphate.
0-(1,1,1-trichloro-2-cyano-2-propyl)-0-ethyl-N-isopropyl phosphoroamidate.
0-(1,1,1-trichloro-2-cyano-2-propyl)-0-ethylphenyl thionophosphonate.
0-(1,1,1-trifluoro-2-cyano-2-propyl)-0-ethyl-S-n-propylthiophosphate.
0-(1,1,1,3,3,3-hexachloro-2-cyano-2-propyl)-0-ethyl-S-n-propylthiophosphate.
0-(1,1,3-trichloro-1,3,3-trifluoro-2-cyano-2-propyl)-0-ethyl-S-n-propylthiophosphate.
0-(2-cyano-2-butyl)-0-ethyl-S-n-propylthiophosphate.
0-(1-cyano-1-cyclopropyl ethyl)-0-ethyl-S-n-propylthiophosphate.
0-(5-chloro-2-cyano-2-pentyl)-0-ethyl-S-n-propylthiophosphate.
0-(1-cyanohexyl)-0-ethyl-S-n-propylthiophosphate.
0-(1-cyanooctyl)-0-ethyl-S-n-propylthiophosphate.
0-(3-methoxy-1-cyanobutyl)-0-ethyl-S-n-propylthiophosphate.
0-(1-cyanocyclohexyl)-0-ethyl-S-n-propylthiophosphate.
0-(1-cyanocyclohexyl)-0-ethyl-S-n-propylphosphorodithioate.
0-(α-cyanobenzyl)-0-ethyl-S-n-propylthiophosphate.
0-(α-cyanobenzyl)-0-ethyl-S-n-butylthiophosphate.
0-(α-cyanobenzyl)-0-ethyl-S-n-propylphosphorodithioate
0-(α-cyano-2-chlorobenzyl)-0-ethyl-S-n-propylthiophosphate.
0-(α-cyano-2-allyloxybenzyl)-0-ethyl-S-n-propylthiophosphate.
0-(α-cyano-2-methylbenzyl)-0-ethyl-S-n-propylthiophosphate.
0-(α-cyano-2-nitrobenzyl)-0-ethyl-S-n-propylthiophosphate.
0-(α-cyano-3-fluorobenzyl)-0-ethyl-S-n-propylthiophosphate.
0-(α-cyano-3-trifluoromethylbenzyl)-0-ethyl-S-n-propylthiophosphate.
0-(α-cyano-4-chlorobenzyl)-0-ethyl-S-n-propylthiophosphate.
0-(α-cyano-2,4-dichlorobenzyl)-0-ethyl-S-n-propylthiophosphate.
0-(α-cyano-2,6-dichlorobenzyl)-0-ethyl-S-n-propylthiophosphate.
0-(α-cyano-3-nitro-2,6-dichlorobenzyl)-0-ethyl-S-n-propylthiophosphate.
0-(α-cyano-2,3,4,5,6-pentafluorobenzyl)-0-ethyl-S-n-propylthiophosphate.
0-(2,4-dichloro-α-cyano-α-methylbenzyl)-0-ethyl-S-n-propylthiophosphate.
0-(2-bromo-1-cyano-3-phenyl-2-propenyl)-0-ethyl-S-n-propylthiophosphate.
0-(α-cyano-2-pyridylmethyl)-0-ethyl-S-n-propylthiophosphate.
0-(α-cyano-6-methyl-2-pyridylmethyl)-0-ethyl-S-n-propylthiophosphate.
0-(α-cyano-1-(2-pyridylethyl)-0-ethyl-S-n-propylthiophosphate.
0-(α-cyano-3-phenoxybenzyl)-0-ethyl-S-n-propylthiophosphate.
0-(α-cyano-3-phenoxybenzyl)-0-ethyl-S-isopropylthiophosphate.
0-(α-cyano-3-phenoxybenzyl)-0-ethyl-S-n-propylphosphordithioate.
0-(α-cyano-3-phenoxybenzyl)-0-ethyl-ethyl-thionophosphonate.
0-(α-cyano-3-(4'-chlorophenoxybenyl)-0-ethyl-S-n-propylthiophosphate.
0-[α-cyano-6-(2,4-dichlorophenoxy)-2-pyridine methyl]-0-ethyl-S-n-propylthiophosphate.
0-(8-cyano-8-pentadecyl)-0-ethyl-S-n-propylthiophosphate.
0-(5-cyano-5-tridecyl)-0-ethyl-S-n-propylthiophosphate.
0-(3-cyano-3-dodecyl)-0-ethyl-S-n-propylthiophosphate.
0-(5-ethoxy-3-cyano-3-pentyl)-0-ethyl-S-n-propylthiophosphate.
0-(α-cyano-3-methylcyclohexyl)-0-ethyl-S-n-propylthiophosphate.
0-(α-cyano-2,4,6-trimethoxybenzyl)-0-ethyl-S-n-propylthiophosphate.
0-(α-cyano-3-(4'-tertbutylphenoxybenzyl)-0-ethyl-S-n-propylthiophosphate.
0-(α-cyano-4-phenoxybenzyl)-0-ethyl-S-n-propylthiophosphate.
0-(α-cyano-4-phenylbenzyl)-0-ethyl-S-n-propylthiophosphate.

The following examples will illustrate the present invention.

EXAMPLE 1

Preparation of 0-(α-cyanobenzyl)-0-ethyl-S-n-propylthiophosphate

A 500 ml four-neck round bottom flask was equipped with a magnetic stirring bar, water condenser, addition funnel and drying tube. The glassware was dried and to this was charged 21.2 grams (0.2 mole) benzaldehyde and 19.5 grams (0.3 mole) potassium cyanide dissolved in 70 ml of water. The reaction flask was cooled to 10°-15° C. using a water/ice bath. To this was added 70 ml of 40% sulfuric acid over a 60 minute period. After the addition was complete, the reaction was allowed to warm to room temperature and stir for an additional two hours. At the end of this time the reaction mixture was extracted with carbon tetrachloride (3×75 ml), washed the combined carbon tetrachloride layers with water (2×50 ml), dried the carbon tetrachloride layer with anhydrous magnesium sulfate, filtered and concentrated to yield benzaldehyde cyanohydrin.

To a 100 ml two-neck round bottom flask equipped with thermometer, water condenser and drying tube, magnetic stirring bar and heating mantel, was charged 5.0 g (0.0376 mole) benzaldehyde cyanohydrin, 3.4 g (0.043 mole) pyridine and 40 ml acetonitrile. The contents were then stirred for two hours at room temperature at which time 7.6 g (0.0376 mole) of 0-ethyl-S-n-propyl phosphorochloridate was added. The mixture was then stirred overnight at room temperature.

The following day a TLC taken of the crude reaction mixture showed that the reaction had not gone to completion. 3.4 g of (0.043 mole) of pyridine was added to the flask and the reaction mixture heated to 40° C. for four hours at which time the acetonitrile was removed under vacuum and the residue taken up in 400 ml of ethyl ether and washed with water (2×100 ml). The ether layer is then dried with anhydrous magnesium sulfate, filtered and concentrated under vacuum. The resulting residue is then purified by means of a low pressure liquid chromatography column to yield 2.4 gram of the desired product as an oil. ($n_D^{23}$ 1.5118)

Calcd for $C_{13}H_{18}NO_3PS$: C, 52.16; H, 6.06. Found: C, 52.26; H, 6.05.

EXAMPLE 2

Preparation of
O-(α-cyano-2,3,4,5,6-pentafluorubenzyl)-O-ethyl-S-n-propylthiophosphate A 100 ml round bottom flask fitted with thermometer, water condenser with drying tube and magnetic stirring bar has charged into it 2.8 g (0.033 mole) acetone cyanohydrin, 3 drops triethylamine and 50 ml carbon tetrachloride. The reaction mixture is cooled to 0° C. using a water/ice bath. 5.9 g (0.03 mole) of pentafluoro benzaldehyde is added to the reaction mixture at a rate which allows the temperature to be maintained between 5°–15° C. After all the aldehyde is added the reaction is brought up to room temperature and stirred overnight.

The reaction is cooled to 15° C. (water/ice bath) and 2.4 g (0.03 mole) pyridine is added followed by the addition of 6.0 g (0.03 mole) O-ethyl-S-n-propyl phosphoro chloridate while maintaining a temperature of less than 20° C. After the chloride is added the reaction is brought to room temperature and stirred overnight.

Additional carbon tetrachloride is added to the reaction mixture and then the mixture is washed several times with water, dried over anhydrous magnesium sulfate, filtered and concentrated. The residue is then purified by means of a low pressure liquid chromatography column to yield 1.0 gram of the desired product as an oil ($n_D^{21}$ 1.4720).

Calcd for $C_{13}H_{13}F_5NO_3PS$: C, 40.11; H, 3.37. Found: C, 40.63; H, 3.15.

EXAMPLE 3

Preparation of
O-α-cyano-4-isopropylbenzyl)-O-ethyl-S-n-propylthiophosphate

A 100 ml round bottom flask fitted with thermometer, water condenser with drying tube and magnetic stirring bar has charged into it 6.0 g (0.0405 mole) 4-isopropylbenzaldehyde, 4.8 g (0.0486 mole) trimethylsilyl cyanide, 50 ml methylene chloride and a catalytic amount of triphenyl phosphine and zinc chloride. The material was stirred overnight at room temperature and then transferred to a 250 ml flask at which time 60 ml of 3N hydrochloric acid was added and the mixture stirred for three hours at room temperature. The material was taken up in ethyl ether, dried over anhydrous magnesium sulfate, filtered and concentrated in vacuum.

To 7.2 g (0.041 mole) of the above concentrate dissolved in 50 ml of ethyl ether was added 8.3 g (0.041 mole) 0-ethyl-S-n-propyl phosphorochloridate at 10° C. To this mixture was added 3.6 g (0.045 mole) pyridine while maintaining temperature below 20° C. After the addition of pyridine was complete the reaction was allowed to warm to room temperature and stir over the weekend.

Work-up consisted of filtering off solid (amine salt), washing the ether layer with water, drying the ether layer with anhydrous magnesium sulfate, filtering and concentrating in vacuum. The resulting residue is purified by means of a low pressure liquid chromatography column to yield 1.7 grams of the desired product as an oil ($n_D^{23}$ 1.5055).

Calcd for $C_{16}H_{24}NO_3PS$: C, 59.81; H, 7.48. Found: C, 59.58; H, 7.44.

Examples 4–45 illustrate other compounds of the present invention which were prepared by methods detailed in this invention.

TABLE I

| Example | Nomenclature | Refractive Index (°C.) | Molecular Formula | Calculated (%) C | H | Found (%) C | H |
|---|---|---|---|---|---|---|---|
| 4 | O—(1-Cyanoethyl)-O—ethyl-S—propylthiophosphate | 1.4640 (23) | $C_8H_{16}NO_3PS$ | 40.50 | 6.75 | 39.16 | 6.93 |
| 5 | O—(2,2,2-Trichloro-1-cyanoethyl)-O—ethyl-S—propylthiophosphate | 1.4940 (23) | $C_8H_{13}Cl_3NO_3PS$ | 28.21 | 3.85 | 26.82 | 3.65 |
| 6 | O—(2-Methyl-1-cyanopropyl)-O—ethyl-S—propylthiophosphate | 1.4630 (23) | $C_{10}H_{20}NO_3PS$ | 45.27 | 7.60 | 47.21 | 7.83 |
| 7 | O—(2,2-Dimethyl-1-cyanopropyl)-O—ethyl-S—propylthiophosphate | 1.4500 (25) | $C_{11}H_{22}NO_3PS$ | 47.29 | 7.94 | 47.32 | 8.23 |
| 8 | O—(2-cyano-2-propyl)-O—ethyl-S—propylthiophosphate | 1.4580 (23) | $C_9H_{18}NO_3PS$ | 43.02 | 7.22 | 44.20 | 7.41 |
| 9 | O—(1,1,1-Trichloro-2-cyano-2-propyl)-O—ethyl-S—propylthiophosphate | — | $C_9H_{15}Cl_3NO_3PS$ | 30.48 | 4.26 | 30.08 | 4.07 |
| 10 | O—(1,1,1-Trichloro-2-cyano-2-propyl)-O—ethyl-N—isopropylphosphoroamidate | 1.4755 (23) | $C_9H_{16}Cl_3N_2O_3P$ | 32.02 | 4.78 | 33.07 | 5.05 |
| 11 | O—(1-Cyanocyclohexyl)-O—ethyl-S—propylphosphorodithioate | 1.4362 (25) | $C_9H_{15}F_3NO_3PS$ | 35.41 | 4.95 | 35.32 | 5.51 |
| 12 | O—(1,1,3-Trichloro-1,3,3-trifluoro-2-cyano-2-propyl)-O—ethyl-S—propylthiophosphate | — | $C_9H_{12}Cl_3F_3NO_3PS$ | 26.45 | 2.96 | 27.05 | 3.18 |
| 13 | O—(2-Cyano-2-butyl)-O—ethyl-S—propylthiophosphate | — | $C_{10}H_{20}NO_3PS$ | 45.27 | 7.60 | Residue (50% Pure) | |
| 14 | O—(5-Chloro-2-cyano-2-pentyl)-O—ethyl-S—propylthiophosphate | — | $C_{11}H_{21}ClNO_3PS$ | 42.10 | 6.75 | Residue (80% pure) | |
| 15 | O—(1-Cyanohexyl)-O—ethyl-S—propylthiophosphate | 1.4610 (22) | $C_{12}H_{24}NO_3PS$ | 49.13 | 8.25 | 47.60 | 8.10 |
| 16 | O—(1-Cyanooctyl)-O—ethyl-S—propylthiophosphate | 1.4645 (21) | $C_{15}H_{30}NO_3PS$ | 53.71 | 9.02 | 54.23 | 9.12 |
| 17 | O—(3-Methoxy-1-cyanobutyl)-O—ethyl-S—propylthiophosphate | 1.4615 (21) | $C_{11}H_{22}NO_4PS$ | 44.75 | 7.46 | 45.19 | 7.37 |
| 18 | O—(α-Cyanobenzyl)-O—ethyl-S—butylthiophosphate | 1.5105 (25) | $C_{14}H_{20}NO_3PS$ | 53.66 | 6.43 | 52.44 | 6.61 |
| 19 | O—(α-Cyanobenzyl)-O—ethyl-S—propylphosphorodithioate | 1.5415 (22) | $C_{13}H_{18}NO_2PS_2$ | 49.50 | 5.75 | 48.48 | 5.94 |

TABLE I-continued

| Example | Nomenclature | Refractive Index (°C.) | Molecular Formula | Calculated (%) C | Calculated (%) H | Found (%) C | Found (%) H |
|---|---|---|---|---|---|---|---|
| 20 | O—(α-Cyano-2-nitrobenzyl)-O—ethyl-S—propylthiophosphate | 1.5348 (24) | $C_{13}H_{17}N_2O_5PS$ | 45.34 | 4.98 | 46.57 | 4.90 |
| 21 | O—(α-Cyano-3-fluorobenzyl)-O—ethyl-S—propylthiophosphate | 1.5090 (23) | $C_{13}H_{17}FNO_3PS$ | 49.20 | 5.40 | 50.39 | 5.24 |
| 22 | O—(α-Cyano-3-trifluoromethylbenzyl)-O—ethyl-S—propylthiophosphate | 1.4785 (24) | $C_{14}H_{17}F_3NO_3PS$ | 45.77 | 4.67 | 46.64 | 4.57 |
| 23 | O—(α-Cyano-4-chlorobenzyl)O—ethyl-S—propylthiophosphate | — | $C_{13}H_{17}ClNO_3PS$ | 46.78 | 5.14 | 47.05 | 5.07 |
| 24 | O—(α-Cyano-2,4-dichlorobenzyl)-O—ethyl-S—propylthiophosphate | 1.5412 (22) | $C_{13}H_{16}Cl_2NO_3PS$ | 42.40 | 4.38 | 43.65 | 3.94 |
| 25 | O—(α-Cyano-2,6-dichlorobenzyl)-O—ethyl-S—propylthiophosphate | 1.5370 (21) | $C_{13}H_{16}Cl_2NO_3PS$ | 42.40 | 4.38 | 42.94 | 4.72 |
| 26 | O—(α-Cyano-3-nitro-2,6-dichlorobenzyl)-O—ethyl-S—propylthiophosphate | 1.5550 (21) | $C_{13}H_{15}Cl_2N_2O_5PS$ | 37.78 | 3.66 | 38.10 | 3.24 |
| 27 | O—(2,4-Dichloro-α-cyano-α-methylbenzyl)-O—ethyl-S—propylthiophosphate | 1.5156 (23) | $C_{14}H_{18}Cl_2NO_3PS$ | 43.99 | 4.75 | 41.65 | 4.62 |
| 28 | O—(α-Cyano-2-pyridylmethyl)-O—ethyl-S—propylthiophosphate | — | $C_{12}H_{17}N_2O_3PS$ | 47.99 | 5.71 | 46.27 | 5.74 |
| 29 | O—(α-Cyano-6-methyl-2-pyridylmethyl)-O—ethyl-S—propylthiophosphate | 1.4990 (25) | $C_{13}H_{19}N_2O_3PS$ | 49.67 | 6.09 | 48.10 | 6.47 |
| 30 | O—(α-Cyano-3-phenoxybenzyl)-O—ethyl-S—propylthiophosphate | — | $C_{19}H_{22}NO_4PS$ | 58.30 | 5.67 | 59.02 | 5.69 |
| 31 | O—(α-Cyano-3-phenoxybenzyl)-O—ethyl-S—isopropylthiophosphate | 1.5465 (22) | $C_{19}H_{22}NO_4PS$ | 58.30 | 5.67 | 57.75 | 5.68 |
| 32 | O—(α-Cyano-3-phenoxybenzyl)-O—ethyl-S—propylphosphorodithioate | 1.5595 (24) | $C_{19}H_{22}NO_3PS_2$ | 56.00 | 5.44 | Residue | |
| 33 | O—(α-Cyano-3-phenoxybenzyl)-O—ethyl-ethylthionophosphonate | 1.5550 (22) | $C_{18}H_{20}NO_3PS$ | 59.82 | 5.58 | Residue | |
| 34 | O—(α-Cyano-3-(4'-chlorophenxoybenzyl)-O—ethyl-S—propylthiophosphate | — | $C_{19}H_{21}ClNO_4PS$ | 53.58 | 4.97 | Residue | |
| 35 | O—[α-Cyano-6-(2',4'-dichlorophenoxy)-2-pyridinemethyl]-O—ethyl-S—propylthiophosphate | 1.5478 (23) | $C_{18}H_{19}Cl_2N_2O_4PS$ | 46.86 | 4.15 | 46.86 | 4.20 |
| 36 | O—(1,1,1-Trifluoro-2-cyano-2 propyl)-O—ethyl-S—propylthiophosphate | 1.4362 (25) | $C_9H_{15}F_3NO_3PS$ | 35.41 | 4.92 | 35.32 | 5.51 |
| 37 | O—(α-Cyano-2-bromobenzyl)-O—ethyl-S—propylthiophosphate | 1.5390 (25) | $C_{13}H_{17}BrNO_3PS$ | 41.28 | 4.53 | 41.17 | 4.49 |
| 38 | O—(α-Cyano-3-cyanobenzyl)-O—ethyl-S—propylthiophosphate | 1.5135 (23) | $C_{14}H_{17}N_2O_3PS$ | 51.24 | 5.28 | 51.70 | 5.68 |
| 39 | O—(α-Cyano-3-(benzyloxy)benzyl]-O—ethyl-S—propylthiophosphate | 1.5572 (23) | $C_{20}H_{24}NO_4PS$ | 59.24 | 5.97 | 59.92 | 6.04 |
| 40 | O—(α-Cyano-4-phenylbenzyl)-O—ethyl-S—propylthiophosphate | 1.5790 (23) | $C_{19}H_{22}NO_3PS$ | 60.78 | 5.91 | 60.73 | 5.95 |
| 41 | O—(α-Cyano-4-fluorobenzyl)-O—ethyl-S—propylthiophosphate | 1.4870 (23) | $C_{13}H_{17}FNO_3PS$ | 49.21 | 5.36 | 49.59 | 5.82 |
| 42 | O—(α-Cyano-3-nitrobenzyl)-O—ethyl-S—propylthiophosphate | 1.5366 (23) | $C_{13}H_{17}N_2O_5PS$ | 45.34 | 4.98 | 46.72 | 4.76 |
| 43 | O—(α-Cyano-3-(4'-fluorophenoxybenzyl)-O—ethyl-S—propylthiophosphate | 1.5392 (23) | $C_{19}H_{21}FNO_4PS$ | 55.73 | 5.13 | 56.33 | 5.27 |
| 44 | O—(α-Cyano-3-(4'-methylphenoxybenzyl)-O—ethyl-S—propylthiophosphate | 1.5348 (23) | $C_{20}H_{24}NO_4PS$ | 59.26 | 5.93 | 59.54 | 6.11 |
| 45 | O—(α-Cyano-2,3-dichloro-4-methylbenzyl)-O—ethyl-S—propylthiophosphate | 1.5430 (21) | $C_{14}H_{18}Cl_2NO_3PS$ | 43.98 | 4.71 | 44.42 | 4.69 |

Selected species of the new compounds were evaluated to determine their pesticidal activity against mites, nematodes, and certain insects, including an aphid, a caterpillar, a bettle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The concentrations in parts per million by weight employed in the tests described below were obtained by appropriate dilutions of the stock suspension with water. The test procedures were as follows:

Adults and nymphal stages of the bean aphid (*Aphis fabae* Scop.) reared on potted dwarf nasturtium plants at 65°–70° F. and 50±5 percent relative humidity, constituted the test insects. For testing purposes, the number of aphids per pot was standardized to 100–150 by trimming plants contaning excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50±5 percent, respectively. Aphids which fell onto the paper and were unable to remain standing after being uprighted were considered dead. Aphids remaining on the plants were observed closely for movement and those which were unable to move the length of the body upon stimulation by prodding were considered dead.

Third instar larvae of the southern armyworm (*Spodoptera eridania*, (Cram.)), reared on Tendergreen bean plants at a temperature of 80±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110milliliters of test compound formulation by use of a DeVilbiss spray gun set at 40 psig air pressure. This application, which lasted 25 seconds, was sufficient to wet plants to run-off. As a control, 100–110 millliliters of a water-acetone-emulsifier solution containing no test compound were also sprayed on plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead.

Third instar larvae of the Mexican bean beetle (*Epilachna varivestis*, Muls.), reared on Tendergreen bean plants at a temperature of 80±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 40 psig air pressure. This application, which lasted 25 seconds, was sufficient to wet plants to run-off. As a control, 100–110 milliliters of a water-acetone-emulsifier solution containing no test compound were also sprayed on plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80±5 F. for three days. Although the larvae could easily consume the leaf within 24 to 48 hours, no more food was added. Larvae which were unable to move the length of the body, even upon stimulation, were considered dead.

Four to six day old adult house flies (*Musca domestica*, L.), reared according to the specifications of the Chemical Specialties Manufacturing Association (Blue Book, McNair-Dorland Co., N.Y. 1954; pages 243–244, 261) under controlled conditions of 80±5° F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a soufflé cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80±5° F. and the relative humidity of 50±5 percent. Flies which showed no sign of movement on prodding were considered dead.

Adults and nymphal stages of the two-spotted mite (*Tetranychus urticae* Koch), reared on Tendergreen bean plants at 80±5° F. and 50±5 percent relative humidity were the test organisms. Infested leaves from a stock culture were placed on the primary leaves of two bean plants six to eight inches in height, growing in a two-and-a-half inch clay pot. 150–200 Mites, a sufficient number for testing, transferred from the excised leaves to the fresh plants in a period of twenty-four hours. Following the twenty-four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of water solution containing acetone and emulsifier in the same concentration as the test compound formulation, but containing no test compound, were also sprayed on infested plants. The sprayed plants were held at 80±5° F. and 50±5 percent relative humidity for six days, after which a mortality count of motile forms was made. Microscopic examination for motile forms was made on the leaves of the test plants. Any individual which was capable of locomotion upon prodding was considered living.

Infective migratory larvae of the root-knot nematode, *Meloidogyne incognita* ver. acrita, reared in the greenhouse on roots of tomato (Florida M-1) and cucumber (National pickling), constituted the test organism. This particular nematode incites distinct galls or knots on the roots of certain plants. Infected roots, containing egg masses, were removed from the stock culture and cleaned of soil by shaking and washing with tap water. Roots were finely chopped, then vigorously shaken in a 0.5 percent NaOCl solution for 4 minutes. To separate the nematode eggs from root tissue, the mixture was poured through a 32-mesh sieve nestled in a 500-mesh sieve followed by a gentle stream of water to remove any trace of NaOCl. The trapped eggs were rinsed with water into a 50-ml beaker. Samples of the egg suspension were counted with the aid of a stereoscopic microscope. 4000 to 6000 eggs were added to a series of pint mason jars, each containing 180 cc. of soil. The jars were capped and mixed thoroughly to insure uniform infestation of the soil. The test compounds were formulated by diluting the stock suspension with water to give a suspension containing 3.3 mg of test compound per 10 ml of final formulation which when added to the jar of soil was approximately equal to a rate of 28 kilogram of test compound per acre. Following addition of formulation, the jars were tightly capped, and the contents were thoroughly mixed on a ball mill for five minutes. The jars remained capped for 48 hours after which the contents were transferred to three inch diameter pots. The soil was then planted with cucumber seeds, and since cucumber is susceptible to root-knot nematode attack, it served as an indicator crop. The pots were then placed in a greenhouse. After 4-6 weeks, the cucumber plants were removed from the pots, the roots were washed free of adhering soil, and directly compared with the roots of similar plants grown in infested but untreated soil. The averaged degree of gall formation on the roots of the cucumber plants was the basis for ascertaining nematode control.

The results of these tests are set forth in Table II below. In these tests the pesticidal activity of the compounds at the indicated dosage rate against aphid, mite, Southern Armyworm, Bean Beetle house fly and root-knot nematode was rated as follows:

A = excellent control
B = partial control
C = no control

Dashes indicate no test conducted.

TABLE II

| Example | Bean Aphid | Mite Adult | Mite Egg | Southern Army Worm | Mexican Bean Beetle | House Fly | Root-Knot Nematode |
|---|---|---|---|---|---|---|---|
| 1 | A | A | C | A | C | A | A |
| 2 | A | A | C | A | C | A | — |
| 3 | A | A | C | A | C | A | — |
| 4 | A | A | C | A | A | A | A |
| 5 | C | C | C | C | C | C | — |
| 6 | A | A | C | A | A | A | A |
| 7 | B | C | C | C | C | B | A |
| 8 | A | A | C | A | B | A | A |
| 9 | A | A | C | A | A | A | — |
| 10 | C | C | C | A | C | A | — |
| 11 | C | C | C | C | C | C | — |
| 12 | C | C | C | C | C | A | — |
| 13 | A | A | C | A | C | A | A |
| 14 | A | A | C | A | C | A | — |
| 15 | A | A | C | A | A | A | — |
| 16 | A | A | C | A | C | A | A |
| 17 | A | A | C | B | B | A | — |
| 18 | A | A | C | C | C | A | — |
| 19 | A | A | C | A | C | A | — |
| 20 | A | A | C | A | C | A | — |
| 21 | A | A | C | A | C | A | — |
| 22 | A | A | C | A | C | A | — |
| 23 | A | A | C | A | C | A | — |
| 24 | A | A | B | A | C | A | — |
| 25 | A | A | A | A | A | A | — |
| 26 | A | A | A | A | C | A | — |
| 27 | C | A | C | C | C | C | — |
| 28 | A | A | C | C | C | A | — |
| 29 | A | A | A | A | B | A | — |
| 30 | A | A | A | A | A | A | — |
| 31 | C | A | C | A | B | B | — |
| 32 | C | C | C | C | C | C | — |
| 33 | C | C | C | C | C | C | — |
| 34 | A | A | A | A | A | A | — |
| 35 | A | A | B | A | A | A | — |
| 36 | A | C | C | C | C | A | — |
| 37 | A | A | C | A | C | A | — |
| 38 | A | A | A | A | C | A | — |
| 39 | A | A | A | A | A | A | — |
| 40 | A | A | C | A | A | A | — |
| 41 | A | A | C | A | C | A | — |
| 42 | A | A | A | A | B | A | — |
| 43 | A | A | C | A | A | A | — |
| 44 | A | A | A | A | C | A | — |
| 45 | A | A | C | A | C | A | — |

Southern Corn Rootworm Test

Larvae (6 to 9 days old) of the southern corn rootworm (*Diabrotic Undecim punctate howardi*), constituted the test insects. Germinated corn is used as a food source and as an indicator of feeding inhibition. Rates in this test are based on a 6-inch acre.

One hundred thirty mL of soil that has been partially air dried (4 to 24 hours) and screened through ¼ inch mesh is aliquoted into 10 ounce styrofoam cups. A standard formulation was prepared by weighing 10.4 mg of each compound into 10 mL of acetone containing a constant amount of emulsifier. These formulations were furether diluted with water to produce 100 mL volumes. Ten mL of these formulations (equivalent to 10 lb.±0.5 16" acre) was pipetted onto the surface of the soil. The control cup received 10 mL of water. The next day each cup is shaken 50 times so the chemical is intimately mixed with the soil. The cups are set aside for four days before the larvae and corn are added. On day 4, the lids are removed. Two corn seedlings about 4 days old are placed in the bottom of the cup by tilting the cup and rotating 180° for each seedling placement. Then ten larvae (6 to 9 days old) are added to the surface of the soil. Lids are replaced on the cups and the containers set aside for one week prior to the data recording. The reading for the dead larvae is accomplished by screening the soil through ⅛" mesh or by sprinkling the soil slowly into a metal tray.

Housefly Fumigation Test

Four to six day old adult houseflies (*Musca domestica*, L.), reared according to the specifications of the chemical Specialties Manufacturing Association (Blue Book, McNair-Dorland Co., N.Y. 1954; pages 243-244, 261) under controlled conditions of 80±5° F. and 50±5 percent relative humidity, were the test insects. Ten mg of the compound is dissolved in 10 mL of the standard acetone-triton mixture. A five-milliliter aliquot of this solution is poured into a 60 mm glass Petri dish and the remaining five milliliters are incorporated into 4 ounces of soil. The acetone is allowed to volatilize for 2-4 hours. The soil or the Petri dishes are placed in 8-ounce plastic coated containers (Lilly 86N6BC). A barrier is constructed by stretching a 15 mm by 15 mm piece of cheesecloth across the mouth of the 8-ounce container. The cheesecloth is held in place by inserting a similar container, which has one inch of its bottom removed, into the original container. Three 2-inch pieces of cotton dental roll (No. 2 Johnson & Johnson), saturated in 10% sugar water, are provided above the cheesecloth for the files to feed upon during the holding period. Twenty-five adult houseflies, immobilized by anesthetizing with $CO_2$, are placed on the upper surface of the cheesecloth barrier. The containers are doubled capped with plastic lids (Lilly 8573T) to prevent escape of chemical vapors.

The capped containers are stored at 180±5° F. for 24 hours. Flies unable to move or with toxic symptoms such as spinning or inability to move normally are considered dead. Percent mortality is calculated and compounds with mortality above 50 percent are considered volatile while compounds having mortality below 50 percent are regarded as relatively non-volatile.

Southern Armyworm Systemic Test

Third instar larvae of the southern armyworm (*Spodoptera eridania* (Cram.)) reared on tender green beans in a room where temperature is held at 80±5° F. and relative humidity at 50±5 percent. The test compounds were formulated by diluting the stock suspension with water to give a series of concentrations. Two tender green plants in the primary leaf stage and 6 to 8 inches in height, growing in a three-inch pot containing 200 g of soil are placed in 4 ounce paper container. Twenty milliliters of the test formulation are drenched into the pot. As a control, a similar volume of a water-acetone-emulsifier solution containing no test compound is drenched into another pot with plants. After holding the treated plants for 48 hours at 80±5° F. and 50±5 percent relative humidity, one primary leaf is excised from each plant. The remaining two primary leaves and the trifoliates are excised 7 days after treatment. Each excised leaf is placed in a labeled 9-centimeter Petri dish lined with moistened filter paper. Five randomly selected larvae are introduced into each dish and the dishes are closed and held at 80±5° F. for three days. Although the larvae could easily consume the whole leaf within twenty-four hours, no more food was added. Larvae which were unable to move the length of the body, even upon stimulation by prodding, were considered dead.

TABLE III $$CN-\underset{\underset{CH_3}{|}}{\overset{\overset{CH_3}{|}}{C}}-O-\underset{Y-C_3H_7}{\overset{O\quad O-C_2H_5}{\overset{\|}{P}}}$$

| | | | LD$_{50}$ (ppm) | |
| | | | SOUTHERN | MEXICAN | |
| | | MITE | ARMY | BEAN | HOUSE |
| Y | APHID | ADULT | WORM | BEETLE | FLY |
|---|---|---|---|---|---|
| S | 90 | 43 | 60 | 500 | 57 |
| O | i | i | i | i | i | i = inactive at 500 ppm.

Table III is illustrative of the unexpected broad spectrum increase in pesticidal activity realized by the novel compounds of the instant invention when compared to di-alkoxy compounds of the prior art.

Results realizable in activity when the oxy groups on a pesticidally phosphorous moiety are changed to an oxy group and a thio group are unpredictable and apparently quite specific to the active moiety.

TABLE IV $$\underset{Y}{\overset{C_2H_5O}{\diagdown}}\overset{O}{\underset{\|}{P}}\diagdown_O\diagup\underset{Y}{\overset{O}{\underset{\|}{P}}}\overset{OC_2H_5}{\diagup}$$

| | | | LD$_{50}$ (ppm) | |
| | | | MEXICAN | |
| | | MITE | BEAN | HOUSE |
| Y | APHID | ADULT | BEETLE | FLY |
|---|---|---|---|---|
| C$_3$H$_7$S | i | i | i | i |
| C$_2$H$_5$O | 8 | 6 | 4 | 100 | i = inactive at 500 ppm.

Tetraethyl pyrophosphate (TEPP) (example 2, Table IV) is a commercial product known to be extremely effective against the active stages of mites and other soft-bodied insects. However, the O-ethyl-S-n-propyl analog (example 1, Table IV) was found to be inactive at 500 ppm.

TABLE V

| | Activity Versus Commercial Standards | | | | | Systemic Activity LD$_{50}$(ppm) | |
|---|---|---|---|---|---|---|---|
| | Nematicidal Activity | Soil Insecticide Properties | | | | | |
| | Root-Knot nematode | Southern Corn Rootworm | Phytotoxicity (2500 ppm)* | | | Two Spotted Mite | Southern Army Worm Larvae |
| Structure | ED$_3$(Kg/ha) | LD$_{50}$(lbs/Acre) | Corn | Cotton | Soybean | | |
| CH$_3$–CH(CN)–O–P(=O)(OC$_2$H$_5$)(SC$_3$H$_7$) | 2.4 | 2.3 | 1 | 1 | 1 | — | 30 |
| (CH$_3$)$_2$C(CN)–O–P(=O)(OC$_2$H$_5$)(SC$_3$H$_7$) | 5.0 | 4.0 | — | — | — | ~6 | 40 |
| (CH$_3$)$_2$CH–CH(CN)–O–P(=O)(OC$_2$H$_5$)(SC$_3$H$_7$) | 3.0 | — | — | — | — | 3.5 | 12 |
| CH$_3$–CH(OCH$_3$)–CH$_2$–CH(CN)–O–P(=O)(OC$_2$H$_5$)(SC$_3$H$_7$) | — | 2.1 | — | — | — | — | — |
| 4-Br, 2-Cl-C$_6$H$_3$–O–P(=O)(OC$_2$H$_5$)(SC$_3$H$_7$) (CURACRON) | ~28 | >10 | 3 | 3 | 2 | >100 | >200 |
| 4-CH$_3$S-C$_6$H$_4$–O–P(=S)(OC$_2$H$_5$)(SC$_3$H$_7$) (BOLSTAR) | >28 | >10 | 1 | 1 | 2 | >200 | — |

*Phytotoxicity Ratings: 1 - healthy plant; 5 - dead plant.

Table V illustrates:

(a) the six to ten fold increase in nematicidal activity realizable with the compounds of this invention over that of similarly structured commercial standards;

(b) the greatly increased soil insecticide properties of the cyanohydrin phophates of this invention over similarly structured commercial standards;

(c) the low phytotoxicity relative to other materials possessing the O-ethyl-S-n-propyl phosphorous group; and (d) the outstanding general systemic activity of the cyanohydrin phosphates of this invention compared to similarly structured commercial standards.

TABLE VI

| | Fumigant Activity LD$_{50}$(ppm) | | | | | |
|---|---|---|---|---|---|---|
| | BAIT | | | CONTACT(FUMIGANT)* | | |
| STRUCTURE | Southern Army Worm | Mexican Bean Beetle | House Fly | Southern Army Worm | Mexican Bean Beetle | House Fly |
| CH$_3$–CH(CN)–O–P(=O)(OC$_2$H$_5$)(SC$_3$H$_7$) | 250 | 370 | 7 | 17(+) | 15(+) | 35(+) |
| (CH$_3$)$_2$CH–CH(CN)–O–P(=O)(OC$_2$H$_5$)(SC$_3$H$_7$) | 340 | 500 | 20 | 2(+) | 5(+) | 110(+) |
| CH$_3$O–CH(CH$_3$)–CH$_2$–CH(CN)–O–P(=O)(OC$_2$H$_5$)(SC$_3$H$_7$) | 500 | >500 | 80 | 24(+) | 25(+) | 400(−) |

TABLE VI-continued

| | Fumigant Activity LD$_{50}$(ppm) | | | | | |
|---|---|---|---|---|---|---|
| | BAIT | | | CONTACT(FUMIGANT)* | | |
| STRUCTURE | Southern Army Worm | Mexican Bean Beetle | House Fly | Southern Army Worm | Mexican Bean Beetle | House Fly |
|  | 60 | 500 | 57 | 6(+) | 7(+) | 76(+) |
| 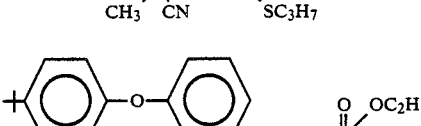 | 250 | 70 | 52 | 180(+) | 30(+) | 350(−) |

*(+) indicates fumigant activity
(−) indicates no fumigant activity
Further evidence for the fumigant activity of the cyanohydrin phosphates of this invention is demonstrated by the fact that

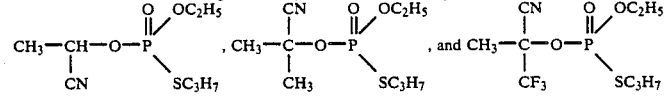

gave positive fumigation response in rice weevil (grain insect) space fumigation tests.

It will be understood that the pest species employed in the above tests are merely representative of a wide variety of plant pests that can be controlled by the use of the compounds of this invention. The compounds contemplated in this invention may be applied as mite ovicides and miticides according to methods known to those skilled in the art. Moreover it has been found that the compounds of the instant invention are useful as fumigants for grain insects, have soil insecticidal activity against the corn root worm, and also possess systemic activity. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not reemulsify the toxicant after it is applied to the plant and wash it off the plant. Nonionic, anionic, amphoteric or cationic dispersing and emulifying agents may be employed; for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by insects, mites and nematodes upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultraviolet light, oxidation, or hydrolysis in the presence of moisture or, at least such decomposition, oxidation, and hydrolysis as would materially decrease the desirable pesticidal characteristic of the toxicants or impart undesirable characteristic for instance, phytotoxicity, to the toxicants. The toxicants are so chemically inert that they are compatible with substantially any other constituents of the spray schedule, and they may be used in the soil, upon the seeds, or the roots of plants without injuring either the seeds or roots of plants. They may also be used in combination with other pesticidally active compounds. When used as miticides they will normally be applied to the foliage of the plants to be treated. It will be appreciated that the compounds of this invention can also be used in combination with other biologically active compounds.

What is claimed is:

1. A pesticidal composition for combatting pests selected from the group consisting of nematodes, insects and mites comprising an acceptable carrier and as the active toxicant a pesticidally effective amount of a compound of the formula:

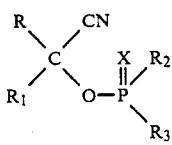

wherein:
X is O or S;
R and $R_1$ are the same or different and are independently hydrogen, lower alkyl ($C_1$-$C_{15}$), whereby $C_3$-$C_{15}$ can be branched or unbranched, and wherein the alkyl chain can be substituted or unsubstituted with alkylthio, alkoxy, or one or more halo; cycloalkyl ($C_3$-$C_8$), alkenyl, phenyl, benzyl, pyridinyl, naphthalene, all of which may be optionally substituted with one or more halogen, nitro, cyano, allyloxy, trihalomethyl, alkyl, alkylthio, alkoxy, or aryloxy, aryloxy alkyl, which can be further substituted with alkoxy, halogen, alkyl, or trihalomethyl groups; taken together R and $R_1$ may form a 5 or 6 membered carbocyclic ring; and $R_2$ and $R_3$ can be the same or different and are independently:
(a) alkylthio ($C_1$-$C_8$),
(b) alkoxy ($C_1$-$C_8$) with the proviso that $R_2$ and $R_3$ may not be alkoxy at the same time, or
(c) alkyl or dialkyl amino;

with the proviso that (1) when $R_2$ and $R_3$ are different and are independently propylthio or ethoxy and when R and $R_1$ are different and are independently trichloromethyl or hydrogen, then X cannot be oxygen; (2) when $R_2$ and $R_3$ are different and are independently propylthio or ethoxy and when R and $R_1$ taken together form a cyclohexyl ring, then X cannot be sulfur; (3) when $R_2$ and $R_3$ are different and are independently propylthio or ethoxy and when R and $R_1$ are different and are independently phenoxyphenyl or hydrogen, then X cannot be sulfur; and (4) when $R_2$ and $R_3$ are different and are independently ethoxy or ethyl and when R and $R_1$ are different and are independently phenoxyphenyl or hydrogen, then X cannot be sulfur.

2. A composition according to claim 1 wherein X is O.

3. A composition according to claim 2 wherein R and $R_1$ are the same or different and are independently hydrogen, lower alkyl ($C_1$-$C_6$), phenyl substituted with aryloxy, further substituted with halogen.

4. A composition according to claim 3 wherein $R_2$ and $R_3$ can be the same or different and are independently alkylthio and alkoxy ($C_1$-$C_8$) with the proviso that $R_2$ and $R_3$ may not be alkoxy at the same time.

5. A composition according to claim 1 wherein the active toxicant is 0-(α-Cyanobenzyl)-0-ethyl-S-n-propylthiophosphate.

6. A composition according to claim 1 wherein the active toxicant is 0-(2-Cyano-2-propyl)-0-ethyl-S-n-propylthiophosphate.

7. A composition according to claim 1 wherein the active toxicant is 0-(2-Methyl-1-cyanopropyl)-0-ethyl-S-propylthiophosphate.

8. A composition according to claim 1 wherein the active toxicant is 0-(α-Cyano-3-2',4'-dichlorophenoxybenzyl)-0-ethyl-S-n-propylthiophosphate.

9. A composition according to claim 1 wherein the active toxicant is 0-(1-Cyanoethyl)-0-ethyl-S-propylthiophosphate.

10. A method of controlling nematodes, insects and mites which comprises subjecting them to a nematocidally, insecticidally or miticidally effective amount of a compound of the formula:

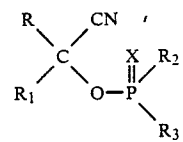

wherein:
X is O or S;
R and $R_1$ are the same of different and are independently hydrogen, lower alkyl ($C_1$-$C_{15}$), whereby $C_3$-$C_{15}$ can be branched or unbranched, and wherein the alkyl chain can be substituted or unsubstituted with alkylthio, alkoxy, or one or more halo; cycloalkyl ($C_3$-$C_8$), alkenyl, phenyl, benzyl, pyridinyl, naphthalene, all of which may be optionally substituted with one or more halogen, nitro, cyano, allyloxy, trihalomethyl, alkyl, alkylthio, alkoxy, or aryloxy, aryloxy alkyl, which can be further substituted with alkoxy, halogen, alkyl, or trihalomethyl groups; taken together R and $R_1$ may form a 5 or 6 membered carbocyclic ring; and $R_2$ and $R_3$ can be the same or different and are independently:
(a) alkylthio ($C_1$-$C_8$),
(b) alkoxy ($C_1$-$C_8$) with the proviso that $R_2$ and $R_3$ may not be alkoxy at the same time, or
(c) alkyl or dialkyl amino;

with the proviso that (1) when $R_2$ and $R_3$ are different and are independently propylthio or ethoxy and when R and $R_1$ are different and are independently trichloromethyl or hydrogen, then X cannot be oxygen; (2) when $R_2$ and $R_3$ are different and are independently propylthio or ethoxy and when R and $R_1$ taken together form a cyclohexyl ring, then X cannot be sulfur; (3) when $R_2$ and $R_3$ are different and are independently propylthio or ethoxy and when R and $R_1$ are different and are independently phenoxyphenyl or hydrogen, then X cannot be sulfur; and (4) when $R_2$ and $R_3$ are different and are independently ethoxy or ethyl and when R and $R_1$ are different and are independently phenoxyphenyl or hydrogen, then X cannot be sulfur.

11. A method according to claim 10 wherein X is O.

12. A method according to claim 11 wherein R and $R_1$ are the same or different and are independently hydrogen, lower alkyl ($C_1$-$C_6$), phenyl substituted with aryloxy, further substituted with halogen.

13. A method according to claim 12 wherein $R_2$ and $R_3$ can be the same or different and are independently alkylthio and alkoxy ($C_1$-$C_8$) with the proviso that $R_2$ and $R_3$ may not be alkoxy at the same time.

14. A method according to claim 12 wherein the compound is 0-(α-Cyanobenzyl)-0-ethyl-S-n-propylthiophosphate.

15. A method according to claim 12 wherein the compound is 0-(2-Cyano-2-propyl)-0-ethyl-S-n-propylthiophosphate.

16. A method according to claim 12 wherein the compound is 0-(2-Methyl-1-cyanopropyl)-0-ethyl-S-propylthiophosphate.

17. A method according to claim 12 wherein the compound is 0-(α-Cyano-3-(2',4'-dichlorophenoxybenzyl)-0-ethyl-S-n-propylthiophosphate.

18. A method according to claim 12 wherein the compound is 0-(1-Cyanoethyl)-0-ethyl-S-propylthiophosphate.

19. A composition according to claim 13 wherein $R_2$ or $R_3$ is a straight chain alkylthio ($C_1$–$C_8$).

20. A composition according to claim 4 wherein said alkylthio is isopropylthio.

21. A method according to claim 13 wherein $R_2$ or $R_3$ is a straight chain alkylthio ($C_1$–$C_8$).

22. A method according to claim 13 wherein said alkylthio is isopropylthio.

* * * * *